(12) United States Patent
Takahashi et al.

(10) Patent No.: US 9,868,764 B2
(45) Date of Patent: Jan. 16, 2018

(54) DIPEPTIDYL PEPTIDASE-IV (DPPIV), INHIBITORY PEPTIDE COMPOUND, COMPOSITION CONTAINING THE SAME, AND PRODUCTION METHOD FOR THE SAME

(71) Applicant: MARUHA NICHIRO CORPORATION, Tokyo (JP)

(72) Inventors: Yoshinori Takahashi, Ibaraki (JP); Akira Kamata, Ibaraki (JP); Tatsuya Konishi, Ibaraki (JP)

(73) Assignee: Maruha Nichiro Corporation, Tokyo (JP)

( * ) Notice: Subject to any disclaimer, the term of this patent is extended or adjusted under 35 U.S.C. 154(b) by 0 days.

(21) Appl. No.: 14/897,891

(22) PCT Filed: May 19, 2014

(86) PCT No.: PCT/JP2014/063238
§ 371 (c)(1),
(2) Date: Dec. 11, 2015

(87) PCT Pub. No.: WO2014/199780
PCT Pub. Date: Dec. 18, 2014

(65) Prior Publication Data
US 2016/0194355 A1    Jul. 7, 2016

(30) Foreign Application Priority Data
Jun. 12, 2013  (JP) ................. 2013-123727

(51) Int. Cl.
| | | |
|---|---|---|
| *A61K 38/00* | (2006.01) | |
| *A61K 38/07* | (2006.01) | |
| *A61K 38/06* | (2006.01) | |
| *C07K 1/12* | (2006.01) | |
| *C07K 5/10* | (2006.01) | |
| *C07K 5/08* | (2006.01) | |
| *C12P 21/06* | (2006.01) | |
| *C07K 5/107* | (2006.01) | |
| *C07K 5/103* | (2006.01) | |
| *C07K 5/083* | (2006.01) | |
| *C07K 14/705* | (2006.01) | |
| *C07K 14/47* | (2006.01) | |
| *C12N 9/48* | (2006.01) | |
| *A23K 20/147* | (2016.01) | |
| *A23L 33/18* | (2016.01) | |

(52) U.S. Cl.
CPC .......... *C07K 5/1016* (2013.01); *A23K 20/147* (2016.05); *A23L 33/18* (2016.08); *C07K 1/12* (2013.01); *C07K 5/0808* (2013.01); *C07K 5/101* (2013.01); *C07K 14/4703* (2013.01); *C07K 14/70596* (2013.01); *C12N 9/485* (2013.01); *C12P 21/06* (2013.01); *A23V 2002/00* (2013.01); *A61K 38/00* (2013.01)

(58) Field of Classification Search
CPC ........ A61K 38/00; A61K 38/07; A61K 38/06; C07K 14/4703; C07K 14/70596; C07K 1/12; C07K 5/0808; C07K 5/10; C07K 5/08; C07K 5/101; C07K 5/1016; C12N 9/485; C12P 21/06
USPC ............... 514/21.9, 20.3, 6.8; 530/330, 331; 435/68.1
See application file for complete search history.

(56) References Cited

U.S. PATENT DOCUMENTS

| | | | |
|---|---|---|---|
| 6,172,043 B1 * | 1/2001 | Ingram | .................. A61K 38/08 514/17.7 |
| 8,586,006 B2 * | 11/2013 | Hood | ................. G01N 33/6845 424/1.11 |
| 2004/0018181 A1 * | 1/2004 | Kufe | .................. C07K 14/4727 424/93.21 |
| 2005/0053606 A1 | 3/2005 | Kufe et al. | |
| 2007/0160631 A1 * | 7/2007 | Jackson | ............... A61K 39/145 424/209.1 |

FOREIGN PATENT DOCUMENTS

| | | |
|---|---|---|
| JP | 3585778 B | 6/2000 |
| JP | 3691685 B | 1/2001 |
| JP | 2004-515472 A | 5/2004 |
| JP | 4357293 B | 1/2005 |
| JP | 2007-039424 A | 2/2007 |

(Continued)

OTHER PUBLICATIONS

Davy, A. et al. "Purification and Characterization of Barley Dipeptidyl Peptidase IV." Plant Physiology, Feb. 2000, vol. 122, pp. 425-431.

(Continued)

*Primary Examiner* — Julie Ha
(74) *Attorney, Agent, or Firm* — Foley & Lardner LLP

(57) ABSTRACT

A peptide compound having a dipeptidyl peptidase-IV (DP-PIV) inhibitory activity or a composition containing the peptide compound that can make a contribution to the prevention of the onset of pathology or the progression in diabetes mellitus patients or those at risk of diabetes mellitus can be provided according to the present invention by a simple method using, as a raw material, milt of a fishery product, which has been eaten for ages and has high safety. In the present invention, a peptide compound having a peptidyl peptidase-IV (DPPIV) inhibitory activity obtained in a hydrolysate of a milt protein source obtained from a fishery product is used as an active component of a composition for inhibiting DPPIV.

15 Claims, 4 Drawing Sheets

(56) References Cited

FOREIGN PATENT DOCUMENTS

| JP | 4915833 B | 2/2007 |
|---|---|---|
| JP | 2008-525430 A | 7/2008 |
| JP | 5068174 B | 7/2008 |
| JP | 4180645 B | 11/2008 |
| JP | 2009-235064 A | 10/2009 |
| JP | 4864064 B | 5/2010 |
| JP | 5176964 B | 4/2013 |
| JP | 2013-212111 A | 10/2013 |
| WO | WO-2011/016220 A | 2/2011 |
| WO | WO-2011/039999 A1 | 4/2011 |

OTHER PUBLICATIONS

Hoffmann et al. "Purification and Analysis of the Major Components of Chum Salmon Protamine Contained in Insulin Formulations Using High-Performance Liquid Chromatography." Protein Expression and Purification, 1990, vol. 1, pp. 127-133.

Kirino, Y. et al. "Increased Plasma Dipeptidyl Peptidase IV (DPP IV) Activity and Decreased DPP IV Activity of Visceral but Not Subcutaneous Adipose Tissue in Impaired Glucose Tolerance Rats Induced by High-Fat or High-Sucrose Diet". Biol. Pharm. Bull, 2009, vol. 32 No. 3, 463-467.

Li-Chan et al. "Peptides Derived from Atlantic Salmon Skin Gelatin as Dipeptidyl-peptidase IV Inhibitors." Journal of Agricultural and Food Chemistry, 2012, vol. 60, pp. 973-978.

McGeachin et al. "Effect of Protamine on Activity of Hog Pancreatic Amylase." Proc. Soc. Exp. Biol. Med., 1962, vol. 109, pp. 556-558.

Sufian et al. "Most Potent Peptides for CCK Release from the enteroendocrine STC-1 cells are derived by peptic hydrolysis from several beans." 64th Annual Meeting of the Japanese Society of Nutrition and Food Science, Tokushima, Japan, May 2010, p. 188.

Takahashi, Y. et al. "Effects of protamine hydrochloride from chum salmon milt on lipid metabolism in rats." Fish Sci., 2011, vol. 77, pp. 1045-1052.

Yazawa, K. Japan Food Science, 2001, vol. 40 No. 12, pp. 61-68.

Office Action dated Mar. 21, 2017 in related Korean Appl. No. 10-2016-7000641 with partial English-language translation (7 pgs.).

PubChem Peptide Substance ID No. 29981290 published Dec. 4, 2007 (available at https://pubchem.ncbi.nlm.nih.gov/substance/29981290).

PubChem Peptide Substance ID No. 32886295 published Dec. 5, 2007 (available at https://pubchem.ncbi.nlm.nih.gov/substance/32886295).

PubChem Peptide Substance ID No. 32958575 published Dec. 4, 2007 (available at https://pubchem.ncbi.nlm.nih.gov/substance/32958575).

* cited by examiner

SEQUENCE LISTING

```
<160> NUMBER OF SEQ ID NOS: 3

<210> SEQ ID NO 1
<211> LENGTH: 4
<212> TYPE: PRT
<213> ORGANISM: Oncorhynchus keta
<220> FEATURE:
<223> OTHER INFORMATION: Peptide inhibitor against dipeptidyl peptidase
      IV

<400> SEQUENCE: 1

Phe Pro Val Gly
1

<210> SEQ ID NO 2
<211> LENGTH: 4
<212> TYPE: PRT
<213> ORGANISM: Oncorhynchus keta
<220> FEATURE:
<223> OTHER INFORMATION: Peptide inhibitor against dipeptidyl peptidase
      IV

<400> SEQUENCE: 2

Leu Pro Val Leu
1

<210> SEQ ID NO 3
<211> LENGTH: 4
<212> TYPE: PRT
<213> ORGANISM: Oncorhynchus keta
<220> FEATURE:
<223> OTHER INFORMATION: Peptide inhibitor against dipeptidyl peptidase
      IV

<400> SEQUENCE: 3

Val Pro Phe Pro
1
```

DIPEPTIDYL PEPTIDASE-IV (DPPIV), INHIBITORY PEPTIDE COMPOUND, COMPOSITION CONTAINING THE SAME, AND PRODUCTION METHOD FOR THE SAME

TECHNICAL FIELD

The present invention relates to peptides having a dipeptidyl peptidase-IV (DPPIV) inhibitory activity and salts thereof (as peptide compounds), and compositions containing the same. The compositions contain, as an active ingredient, one or more of the peptide compounds having a DPPIV inhibitory activity, which are found in hydrolysates of protein sources derived from milts of fishery products such as fish and shellfish.

BACKGROUND ART

Diabetes mellitus includes a group of metabolic diseases having a cardinal symptom of chronic hyperglycemia based on insufficient insulin action. Glycemic control performed for the treatment is very significant as means for suppressing not only the onset of diabetes mellitus but also the onset and progression of complications such as retinopathy, nephropathy, neuropathy, cardiac infarction and brain infarction; and for improving the quality of life (QOL) and life expectancy of a patient. In Japan, 95% or more of diabetes mellitus patients are presumed to be type 2 diabetes mellitus (non-insulin dependent diabetes mellitus) patients. Recent years, a dipeptidyl peptidase-IV (DPPIV) inhibitor has been approved as a novel therapeutic agent for type 2 diabetes mellitus, and has attracted attention because it causes a small adverse reaction such as hypoglycaemia and can perform glycemic control with an excellent mechanism. The DPPIV converts incretin (gastric inhibitory polypeptide: GIP, glucagon-like peptide-1: GLP-1), which is a gastrointestinal hormone to stimulate insulin secretion by acting on pancreatic β cells, to its inactive type. Therefore, when the DPPIV is inhibited, the action of incretin can be retained to promote insulin secretion. The DPPIV is one of serine proteases, and is an enzyme that recognizes and cuts proline (Pro) or alanine (Ala) at the second site from the N-terminal of a peptide. It has been reported that the DPPIV acts strongly on peptides having proline and alanine at the second residue from the N-terminal, and further having lysine (Lys) and arginine (Arg) as the N-terminal residue (Non Patent Literature 1).

An inhibitory effect to increase of blood glucose level by protein hydrolysates has been reported. As the mechanisms of this action, an action to promote insulin secretion (Patent Literature 1), a glucose absorption inhibitory activity (Patent Literature 2), and promotion of glucagon-like peptide-1 (GLP-1) secretion (Patent Literature 3) have been reported. In some reports, inhibitory effect to increase of blood glucose level was recognized by an enzymatically decomposed product of layer (Patent Literature 4) and a peptide obtained by decomposing royal jelly (Patent Literature 5). There are some reports, in which no mechanisms were revealed. As a product obtained from milt of a fishery product as a starting material, protamine extracted from milt is known to have an amylase inhibitory activity (Non Patent Literature 2) and an action to promote GLP-1 secretion (Non Patent Literature 3).

Many compounds obtained by chemically synthesis have been reported by paying attention to the DPPIV inhibitory activity (Patent Literature 6), but such chemically synthesized products should be used carefully in consideration of a safety problem and an adverse reaction. As the DPPIV inhibitors derived from natural products, those are known such as peptides derived from a water-soluble fraction of cheese (Patent Literature 7), peptides derived from a milk protein (Patent Literature 8), enzymatically decomposed products of an azuki bean or a kidney bean (Patent Literature 9), peptides derived from gelatin (Patent Literature 10), and peptides derived from enzymatically decomposed products of gelatin extracted from a salmon skin (Non Patent Literature 4), etc.

Milt of a fishery product has a lower use value than eggs thereof, and has been not effectively used. Their uses are limited to a fertilizer or a feed. Even milt derived from salmon, which is comparatively well used, is used as a starting material of protamine or a nucleic acid, but the milt is disposed as industrial waste in an amount of 10,000 tons or more per year.

REFERENCE LIST

Patent Literature

Patent Literature 1: JP4864064B
Patent Literature 2: JP2009-235064A
Patent Literature 3: JP4180645B
Patent Literature 4: JP3585778B
Patent Literature 5: JP3691685B
Patent Literature 6: JP4357293B
Patent Literature 7: JP4915833B
Patent Literature 8: JP5068174B
Patent Literature 9: WO2011/016220
Patent Literature 10: JP5176964B
Patent Literature 11: US2005/0053606A

Non Patent Literature

Non Patent Literature 1: Plant Physiol., Vol. 122, 425-432
Non Patent Literature 2: Proc. Soc. Exp. Biol. Med., Vol. 109, 556-558
Non Patent Literature 3: Proceedings of the 64th Annual Meeting of the Japan Society of Nutrition and Food Science, p. 188
Non Patent Literature 4: J. Agric. Food Chem., Vol. 60, 973-978
Non Patent Literature 5: Protein Expression and Purification, Vol. 1, 127-133

SUMMARY OF INVENTION

Technical Problem to be Solved by the Invention

An object of the present invention is to provide a peptide compound having a DPPIV inhibitory activity or a composition containing the peptide compound that can make a contribution to the prevention of the onset of pathology or the progression in diabetes mellitus patients or those at risk of diabetes mellitus by a simple method using milt of a fishery product, as a raw material, with experience of eating them for ages and with high safety. Another object of the present invention is to provide DPPIV inhibitory active components for food and drink, which have an inhibitory effect to increase of blood glucose level, such as functional food products, health-promoting food products, food products for special dietary uses, nutritional supplements, health assistant food products and supplements, by a simple method using milt of a fishery product, as a raw material, with experience of eating them for ages and with high safety.

Means for Solving the Problems

The present inventors have made earnest studies on a naturally-derived material having DPPIV inhibitory activity, and, thus, the present inventors have found that a hydrolysate of a protein source from milt or milt of a fishery product or processed milt has DPPIV inhibitory activity. Subsequently, the present inventors have determined the structure and/or the novel peptides having a DPPIV inhibitory activity contained in the hydrolysate and, then, accomplished the present invention.

The first embodiment of a composition for inhibiting DPPIV according to the present invention is characterized in comprising a peptide compound(s) having a DPPIV inhibitory activity obtained by hydrolysis of a protein source derived from milt of a fishery product.

The second embodiment of a composition for inhibiting DPPIV according to the present invention is characterized in comprising as a DPPIV inhibiting component, at least one selected from Phe-Pro-Val-Gly (SEQ ID NO: 1) or salts thereof, Ile-Pro-Leu or salts thereof, Leu-Pro-Val-Leu (SEQ ID NO: 2) or salts thereof, and Val-Pro-Phe-Pro (SEQ ID NO: 3) or salts thereof.

Such a composition for inhibiting DPPIV or a peptide compound can be used for preparing pharmaceuticals; food and drink, such as functional food products, health-promoting food products, food products for special dietary uses, nutritional supplements, health assistant food products and supplements, etc.; pet foods etc. for inhibiting DPPIV.

The peptide compound(s) according to the present invention is at least one selected from Phe-Pro-Val-Gly (SEQ ID NO: 1) and salts thereof; Ile-Pro-Leu and salts thereof; Leu-Pro-Val-Leu (SEQ ID NO: 2) and salts thereof. One of these peptide compounds may be used singly or used in the form of a mixture of two or more of these for desired usage.

A method of producing a hydrolysate having a DPPIV inhibitory activity according to the present invention comprises a step of hydrolyzing a protein source derived from milt of a fishery product to obtain the hydrolysate having a DPPIV inhibitory activity.

A method of producing a peptide compound having a DPPIV inhibitory activity according to the present invention comprises a steps of hydrolyzing a protein source derived from milt of a fishery product to obtain a hydrolysate containing the peptide compound having a DPPIV inhibitory activity; and a step of isolating the peptide compound having a DPPIV inhibitory activity from the hydrolysate.

There have been no reports disclosing that DPPIV inhibition was recognized in processed products from milt as a raw material. Among the peptides determined according to the present invention, their structures and activities of Phe-Pro-Val-Gly (SEQ ID NO: 1), Ile-Pro-Leu and Leu-Pro-Val-Leu (SEQ ID NO: 2) have been not reported. Although Val-Pro-Phe-Pro (SEQ ID NO: 3) is known to inhibit the action of pan-epithelial membrane mucin (MUC1) pertaining to the growth of cancer cells (Patent Literature 11), its DPPIV inhibition activity was unknown.

As the inhibitory effect to increase of blood glucose level provided by a material derived from milt, an amylase inhibitory activity of protamine extracted from milt is known (Non Patent Literature 2). However, when the DPPIV inhibitory peptide of the present invention having an amino acid sequence of Phe-Pro-Val-Gly (SEQ ID NO: 1), Ile-Pro-Leu, Leu-Pro-Val-Leu (SEQ ID NO: 2) or Val-Pro-Phe-Pro (SEQ ID NO: 3) is compared with the amino acid sequence of protamine, it is clear that the DPPIV inhibitory peptide of the present invention is not derived from protamine (Non Patent Literature 5).

In addition, it was reported that a peptide derived from an enzymatically decomposed product of gelatin extracted from a salmon skin has a DPPIV inhibitory activity when a protein hydrolysate derived from a fishery product was used as a raw material (Non Patent Literature 4). However, milt and skin collagen are largely different in the amino acid composition. Therefore, it is clear that the difference peptide groups each other are the activity centrals regarding the DPPIV inhibitory activities of the compositions obtained by hydrolysis.

A collagen extraction process from the skin and a complicated process to remove contaminated lipid contained in the skin or impurities from the other tissues are necessary to obtain a hydrolysate of skin collagen. Since the skin and the milt are clearly the different parts, no skin collagen is contained in milt. Since milt has a shape apparently different from the other parts, it is considered that sorting of each milt as a row material can be easily performed. Since milt has a small lipid content, milt is considered to be suitable as a raw material. Nucleic acids are released by hydrolysis of milt etc. and its excellent taste becomes apparent. Therefore, milt is considered to be applicable widely in the field of food.

Effects of the Invention

A peptide compound having DPPIV inhibitory activity and a composition containing the peptide compound according to the present invention has high safety, because their raw materials are milt of a fishery product(s), which has been eaten for ages. Therefore, they can be widely used for pharmaceuticals, food and drink, (such as functional food products, health-promoting food products, food products for special dietary uses, nutritional supplements, health assistant food products and supplements), pet food, etc.

In addition, milt of a fishery product can be used as a raw material to obtain the peptide compound having a DPPIV inhibitory activity and the composition containing the peptide compound according to the present invention.

Particularly, salmon milt is preferably used, because
   a small amount of salmon milt is used for food;
   salmon milt has few main applications other than the raw material for functional food products such as protamine and/or DNA; and
   salmon milt has been disposed as industrial waste in an amount of 10,000 tons or more per year.

Furthermore, salmon milt having low maturity, which is not used even for production of protamine and DNA, can be used as the raw material in the present invention. As the other raw material, a by-product obtained after extraction of protamine and/or DNA as a functional material from salmon milt can be used. In this manner, the raw materials for the present invention are inexpensively and stably available, and, therefore, the present invention can make a contribution to effective utilization of unused resources and reduction of industrial waste.

DESCRIPTION OF EMBODIMENTS

Figure 1:
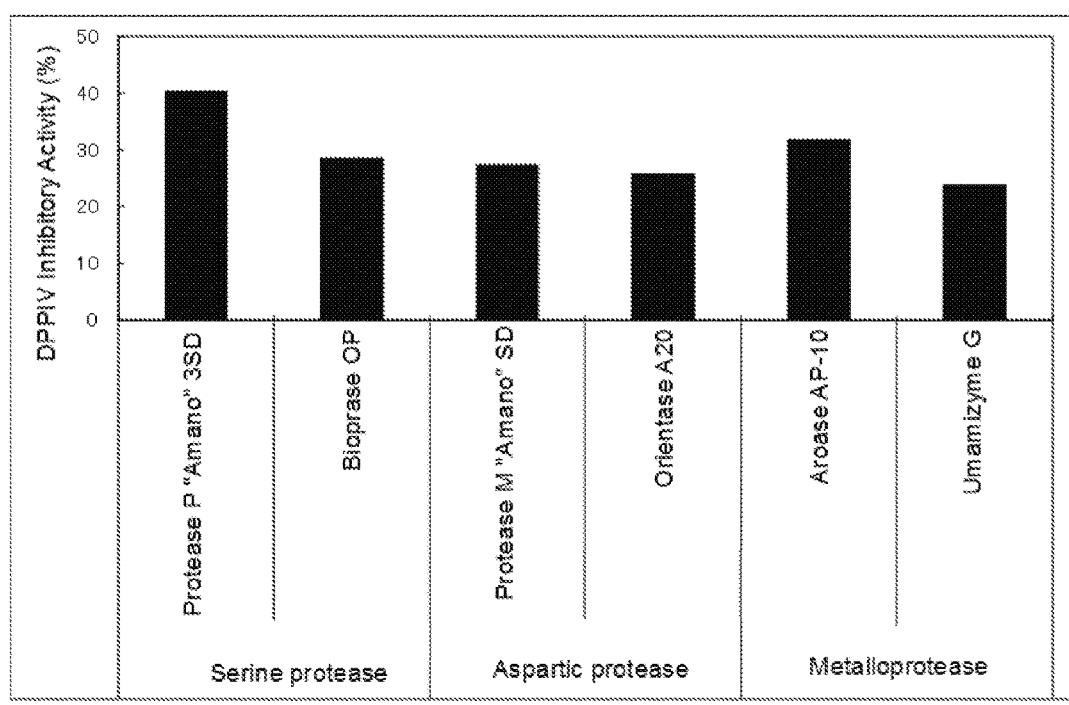
FIG. 1 illustrates the measurement results of DPPIV inhibitory activity of hydrolysates obtained in Example 1.

A composition having a DPPIV inhibitory activity of the present invention comprises, as a component having a DPPIV inhibitory activity, a peptide compound obtained from a hydrolysate of a protein source contained in milt of a fishery product (namely, a testis of a fishery product). The hydrolysate can be obtained by hydrolyzing the protein source derived from milt of a fishery product(s) under a condition where the peptide compound having a DPPIV inhibitory activity is produced.

The composition containing the peptide compound having a DPPIV inhibitory activity can be in any of the following forms:

(1) A hydrolysate comprising a peptide compound having a DPPIV inhibitory activity obtained by hydrolyzing a protein source derived from milt of a fishery product(s) such as fish and shellfish.

(2) A fraction, a crude purified product or a purified product having a DPPIV inhibitory activity and comprises one of, or two or more of the peptide compounds having a DPPIV inhibitory activity obtained from a hydrolysate of a protein source derived from milt of a fishery product(s) such as fish and shellfish.

(3) A composition obtained by adding at least one selected from a carrier, an excipient, a diluent and various additives to the hydrolysate, the fraction, the crudely purified product or the purified product having a DPPIV inhibitory activity as described above.

(4) A composition comprising one or more peptide compounds isolated from a hydrolysate of a protein source derive from milt of a fishery product(s) such as fish and shellfish.

(5) A composition comprising one or more peptide compounds having a DPPIV inhibitory activity obtained by synthesis using the amino acid sequence of any of the above-described isolated peptide compounds.

(6) A composition obtained as a mixture of two or more peptide compounds having a DPPIV inhibitory activity.

(7) A composition obtained by adding at least one selected from a carrier, a excipient, a diluent and various additives to any one of the compositions of (4) to (6) described above.

The fraction, the crude purified product or the purified product having a DPPIV inhibitory activity described in (2) above can be obtained by:

a method of obtaining a fraction(s) including a peptide compound(s) having a DPPIV inhibitory activity by carrying out a fractionation, etc., by ultrafiltration, a membrane treatment, a liquid separation, separation with resin after hydrolysis treatment of the protein source derived from milt of a fishery product(s) such as fish and shellfish; or a method of purifying the fraction(s) as described above by various separation and/or purification methods.

For example, a fraction containing a peptide compound(s) having a DPPIV inhibitory activity obtained by removing polymer compounds from the hydrolysis of the milt-derived protein source is subjected to a purifying treatment if necessary, and, then to a drying treatment by lyophilization, etc. Thus, a composition containing the peptide compound(s) having a DPPIV inhibitory activity can be obtained in a powder form. The removal of the polymer compounds may be performed so that polymer compounds having a molecular weight of at least 5000 or more can be removed.

Examples of the peptide compound having a DPPIV inhibitory activity include respective peptides and salts thereof whose DPPIV inhibitory activity is confirmed in Example 7 and Example 9 described below, and at least one of these can be used as an active component for providing a composition for inhibiting DPPIV of the present invention. Preferable examples of the peptide compound contained in the composition of the present invention include the following four peptides and salts thereof:

(A) A peptide having an amino acid sequence of FPVG (Phe-Pro-Val-Gly, SEQ ID NO: 1) or a salt thereof.

(B) A peptide having an amino acid sequence of IPL (Ile-Pro-Leu) or a salt thereof.

(C) A peptide having an amino acid sequence of LPVL (Leu-Pro-Val-Leu, SEQ ID NO: 2) or a salt thereof.

(D) A peptide having an amino acid sequence of VPFP (Val-Pro-Phe-Pro, SEQ ID NO: 3) or a salt thereof As the protein source derived from milt of a fishery product used as the raw material for the hydrolysis, milt itself of a fishery product, a protein source extracted from milt of a fishery product, etc. can be used. As the protein source extracted from milt of a fishery product, a by-product obtained during production of protamine and/or DNA from milt of a fishery product can be used. The method of producing protamine and/or DNA is not especially limited. Regarding the protamine production, for example, milt of a fishery product is ground, and such components can be extracted therefrom into a mineral acid aqueous solution. Regarding the DNA production, milt of a fishery product is ground, if necessary, and DNA can be obtained by a hydrolysis treatment using protease or nuclease, or by an extraction treatment using a saline aqueous solution, an alkaline aqueous solution, an organic solvent, a surface active agent, etc. The by-product is a residual (or a residue) obtained after extracting or separating protamine and/or DNA from milt of a fishery product, and, as the raw material of the hydrolysis, the residual itself, an extract or a concentrate containing an active component(s) extracted or concentrated from the residual, or a protein source further separated therefrom can be used as the raw material for the hydrolysis.

The fishery product is a generic name of aquatic animals classified into chordates, mollusks, echinoderms, arthropods or cnidarians. Examples of the fishery products supplying milt include the fishes such as salmon, trout, etc. belonging to Salmoniformes Salmonidae, tuna, skipjack, etc. belonging to Perciformes Scombridae, yellowtail (young yellowtail), greater amberjack, etc. belonging to Perciformes Carangidae, herring, etc. belonging to Clupeiformes Clupeidae, and pacific cod, etc. belonging to Gadiformes Gadidae, and Cephalopoda such as cuttlefish and octopus. In particular, examples of "salmon" include chum salmon (*Oncorhynchus keta*), silver salmon (*Oncorhynchus kisutch*), sockeye salmon (*Oncorhynchus nerka*), atlantic salmon (*Salmo salar*), king salmon (*Oncorhynchus tshawytscha*), pink salmon (*Oncorhynchus gorbuscha*) and rainbow trout (*Oncorhynchus mykiss*).

As the milt, milt taken out of a fishery product and washed if necessary, or milt washed if necessary and cut or ground can be used for the hydrolysis. Alternatively, a protein source can be extracted from milt by any various extraction methods to be used for the hydrolysis. For example, a protein source contained in a by-product(s) produced as a residual remaining after extraction of protamine and/or DNA from milt can be used for the hydrolysis.

A highly sexually matured milt that contains a large amount of protamine and DNA, but contains a small amount of water, as well as a lowly sexually matured milt that is not suitable to production of protamine and DNA because of small contents of protamine and DNA and a large content of water can be used as the raw material for the hydrolysis. The water content of milts of general salmons are approximately 70 to 85%, and depending on the purpose, the sexual maturity degree of a milt can be defined in terms of the water content therein. According to the present invention, a wide range of milts including, for example, highly sexually matured milts having a water content smaller than 75% and lowly sexually matured milts having a water content of 75% or more can be used as the raw material.

One or more of the melts from the different fishery products can be used in a mixture. A protein source(s) other than the milt can be mixed with the protein source of the milt to be used as the raw material for the hydrolysis. As the protein source other than the milt, at least one of microorganisms, plants, animals, fermentation products from these, and protein sources extracted therefrom, etc. can be used in accordance with the purpose of the present invention.

The hydrolysis of the protein source derived from milt of a fishery products can be carried out by means known in the related art. For example, an acid, an enzyme, etc. can be used, but the method is not restricted. Examples of enzymes that hydrolyze a protein source include an endopeptidase and an exopeptidase, and one of these can be singly used or these can be used in combination. Preferably, an enzyme mainly containing an endopeptidase is used. Examples of the endopeptidase include serine proteases, aspartic proteases, metalloproteases and cysteine proteases, and an enzyme mainly containing a serine protease(s) is preferably used. Two or more of such enzymes hydrolyzing a protein source can be used in combination. Preferably, an enzyme(s) that hydrolyzes a protein source is added to a raw material of a milt protein source in a concentration of 0.001 to 5% (w/w) and reacted for 1 to 48 hours at a temperature and pH suitable to the hydrolytic activity thereof. Alternatively, a purified enzyme preparation and a crude enzyme preparation can be used, as well as an enzyme activity derived from milt as the raw material can be utilized.

The hydrolysis reaction is conducted under the reaction condition where a water-soluble peptide compound(s) having a DPPIV inhibitory activity can be obtained in a resultant hydrolysate. The reaction condition can be obtained, for example, by the following method:

First, a decomposition reaction of a protein source of a raw material is performed, and sampling of reaction products at prescribed time intervals in accordance with the progress of the reaction is carried out. The DPPIV inhibitory activity of each of the reaction products thus obtained is measured, and a reaction condition to obtain a reaction product having the desired DPPIV inhibitory activity is specified. The reaction condition thus specified is employed as a reaction condition for producing the hydrolysate. As the reaction condition, a reaction condition under which both IP (Ile-Pro) and VPL (Val-Pro-Leu) are contained in the hydrolysate is preferably selected. Furthermore, a reaction condition under which at least one of the peptide compounds (A) to (D) described above in addition to the above two peptides can be also obtained in the hydrolysate is more preferably selected.

The term "peptide" as used herein refers to an amino acid polymer having a peptide bond(s), and the number of amino acid residues contained in the peptide is not limited as long as it is 2 or more, and even a protein is included in this term.

In the examples, etc. described below, a composition containing two or more peptides is designated as a "peptide composition". Besides, a "protein source" includes a protein itself and a protein complex formed by a protein and a lipid and/or sugar, etc.

In the hydrolysate of the protein source derived from milt of a fishery product(s), peptide compounds having various lengths (molecular weights) and amino acid sequences can be obtained in a mixed state depending on the type of the protein source and the condition for the hydrolysis reaction. On the other hand, nucleic acid, etc. are released into the hydrolysate by hydrolyzing milt of a fishery product and, thus, the hydrolysate exhibits excellent taste. Therefore, the hydrolysate can be widely used in the field of food.

The isolation of a peptide compound(s) having a DPPIV inhibitory activity from the hydrolysate can be performed by a known separation method, and, for example, a method using a separation column described in Example 5 below can be suitably used.

A DPPIV inhibitor can be prepared by using, as an active component, one or more selected from a composition containing a hydrolysate having a DPPIV inhibitory activity of the present invention and peptide compounds extracted from the hydrolysate in unchanged form, or if necessary, together with a carrier, an excipient, a diluent, etc. Alternatively, one or more selected from a composition containing a hydrolysate having a DPPIV inhibitory activity of the present invention and peptide compounds extracted from the hydrolysate can be contained in pharmaceuticals; food and drink (such as functional food products, health-promoting food products, food products for special dietary uses, nutritional supplements, health assistant food products and supplements, etc), pet foods etc., in order to provide a DPPIV inhibitory activity thereto.

An example of the hydrolysate of a protein source derived from milt of a fishery product includes a hydrolysate containing at least IP (Ile-Pro) and VPL (Val-Pro-Leu), and the hydrolysate preferably contains, in addition to these two peptides, at least one selected from FPVG (Phe-Pro-Val-Gly, SEQ ID NO: 1), IPL (Ile-Pro-Leu), LPVL (Leu-Pro-Val-Leu, SEQ ID NO: 2) and VPFP (Val-Pro-Phe-Pro, SEQ ID NO: 3). Each of these peptides may be in the form of a salt.

The acids forming the salts are not especially limited, and regarding the use for pharmaceuticals, food and drink, pet foods, etc., the following pharmaceutically acceptable salts are preferred:

Examples of acid addition salts include hydrochloride, sulfate, nitrate, methanesulfonate, p-toluenesulfonate, phosphate, salts of tricarboxylic acids such as citric acid, salts of dicarboxylic acids such as oxalic acid, malonic acid, succinic acid, malic acid, maleic acid or fumaric acid, and salts with monocarboxylic acids such as acetic acid, propionic acid, butyric acid or lactic acid. Next, bases forming the salts is not especially limited, and regarding the use for pharmaceuticals, food and drink, pet foods, etc., the bases forming the following pharmaceutically acceptable salts are preferred:

Examples include inorganic salts such as sodium salts, potassium salts, calcium salts, magnesium salts, ammonium salts, lithium salts, aluminum salts and strontium salts, and organic salts such as mono-, di- and tri-alkylamine salts like methylamine salts, dimethylamine salts and triethylamine salts, mono-, di- and tri-hydroxyalkylamine salts, guanidine salts and N-methylglucosamine salts.

Ratios of IP, VPL, IPL, and LPVL (SEQ ID NO: 2) contained in the hydrolysate (in the solid content) are preferably in the following ranges:

Ile-Pro (IP): 0.001 to 10% by weight
Val-Pro-Leu (VPL): 0.001 to 5% by weight
Ile-Pro-Leu (IPL): 0.001 to 1% by weight
Leu-Pro-Val-Leu (LPVL, SEQ ID NO: 2): 0.001 to 1% by weight The hydrolysate containing the two or more peptides described above can be obtained by setting the condition for the hydrolysis of the protein source derived from milt of a fishery product(s) so that these peptides or salts thereof can be contained in the hydrolysate in the above-described ranges. When cuttlefish milt is used, the content of IP is preferably 0.005 to 5% by weight.

Preferable examples of the hydrolysate include those having the composition as shown in Table 1 below obtained by the same treatment as that for the hydrolysate as the peptide composition in Example 1 using a salmon milt:

TABLE 1

| Sequence No. | Peptide Compound | Mg per g of Product (Whole Composition): Lower Limit | Mg per g of Product (Whole Composition): Upper Limit |
|---|---|---|---|
| 1 | Phe-Pro-Val-Gly (SEQ ID NO: 1) | 0.001 | 5 |
| 2 | Ile-Pro-Leu | 0.0001 | 5 |
| 3 | Leu-Pro-Val-Leu (SEQ ID NO: 2) | 0.0001 | 5 |
| 4 | Val-Pro-Phe-Pro (SEQ ID NO: 3) | 0.001 | 1 |
| 5 | Ile-Pro | 0.0001 | 20 |
| 7 | Val-Pro-Ile | 0.0001 | 1 |
| 8 | Val-Pro-Leu | 0.0001 | 10 |
| 9 | Ile-Pro-Ile | 0.0001 | 1 |
| 10 | Leu-Pro-Leu | 0.001 | 1 |
| 11 | Leu-Pro-Phe | 0.001 | 5 |

The peptide composition can be added, as it is, to pharmaceuticals; food and drink (such as functional food products, health-promoting food products, food products for special dietary uses, nutritional supplements, health assistant food products and supplements, etc.), pet foods etc., in order to obtain the DPPIV inhibitory effect intended by the present invention. The purity of the peptide composition can be increased by a fractionation treatment by ultrafiltration, a membrane treatment, a liquid separation operation or a fraction treatment with resin etc. The synthesized peptide compounds can be also used. The peptide compound can be formed in a powder form by lyophilization or spray-drying, etc. after increase of the purity of the active peptide(s). The peptide compounds or the composition having a DPPIV inhibitory activity of the present invention can be orally administered to inhibit DPPIV in a living body, so as to lower the blood glucose level.

Regarding formulation of the composition for DPPIV inhibition according to the present invention, when a peptide or its salt can be directly formulated, at least one of the peptides and the salts thereof having a DPPIV inhibitory activity can be used for formulation, as it is. On the other hand, when formulation is performed by using at least one of carriers, excipients and diluents, the formulation can be conducted by using at least one of carriers, excipients and diluents, which are acceptable pharmaceutically or as the additives for food; and either at least one of peptides having a DPPIV inhibitory activity and salts thereof, or a composition comprising at least one of the peptides having a DPPIV inhibitory activity and the salts thereof; as well as, various additives such as a vitamin, a colorant, a seasoning agent, a sweetening agent and an antioxidant added if necessary. A combination ratio of at least one of the peptides having a DPPIV inhibitory activity and salts thereof contained in the formulation can be selected from the range of 0.0001 to 100% by weight.

For measuring a DPPIV inhibitory activity, a commercially available kit or the other means can be used. For, example, DPPIV Drug Discovery Assay Kit (manufactured by Enzo Life Sciences, Inc.) can be used.

Now, the present invention will be explained more in detail by showing the example below, but it is noted that the examples are merely the embodiments and do not limit the present invention.

EXAMPLES

Example 1

Production of DPPIV Inhibitory Peptide Composition from Salmon Milt

Milt of chum salmon (*Oncorhynchus keta*) was ground, water was added to 8 g of the ground product (water content of 77.0%), and the resultant mixture was adjusted to an optimum pH of each enzyme. As the enzyme that hydrolyzes a protein source, Protease P "Amano" 3SD (derived from *Aspergillus melleus*, manufactured by Amano Enzyme Inc.) and Bioprase OP (derived from *Bacillus clausii*, manufactured by Nagase Chemtex Corporation) were used as a serine protease, Protease M "Amano" SD (derived from *Aspergillus oryzae*, manufactured by Amano Enzyme Inc.) and Orientase A20 (derived from *Aspergillus niger*, manufactured by HBI Enzymes Inc.) were used as an aspartic protease, Aroase AP-10 (derived from *Bacillus subtilis*, manufactured by Yakult Pharmaceutical Industry Co., Ltd.) and Umamizyme G (derived from *Aspergillus oryzae*, manufactured by Amano Enzyme Inc.) were used as a metalloprotease, and Papain DF was used as a cysteine protease, respectively. After heating each resultant mixture to an optimum temperature of each enzyme, 0.02 g of the enzyme was added thereto, followed by stirring for 4 hours, so as to carry out each enzymatic decomposition reaction. The reaction solution thus obtained was heated to 90° C. to inactivate the enzyme. After cooling, the resultant solution was filtered thought Celite. The filtrate was allowed to pass through an ultrafiltration membrane for removing a fraction of a molecular weight of 5,000 or more, and the resultant filtrate was freeze-dried to obtain a powder of a DPPIV inhibitory peptide composition. Since the molecular weight of DNA contained in milt is several tens of thousands or more, it is presumed that high molecular weight DNA could be extracted and removed through these treatments.

Example 2

Measurement of DPPIV Activity

Each of the DPPIV inhibitory peptide compounds obtained in Example 1 was measured for the DPPIV inhibitory activity. The measurement was performed by using a partly modified DPPIV Drug Discovery Assay Kit (manufactured by Enzo Life Sciences, Inc.). As a substrate of a DPPIV enzyme, an AMC substrate (H-Gly-Pro-amino-4-methylcoumarin, BML-P189-9090; manufactured by Biomol) was used, as an enzyme, DPPIV (Human, recombinant; manufactured by Biomol) was used, and as a control inhibitor, Diprotin A (manufactured by Peptide Institute Inc.) was used. Specifically, in a 96-well plate, 25 µL of a 50 mM Tris buffer (pH 7.5), 10 µL of a hydrolysate aqueous solution (3 mg/mL) obtained after removing the fraction of the high molecular compounds in Example 1, and 15 µL of a DPPIV (0.002 mU/µL) solution were added and mixed, and the resultant solution was pre-incubated at 37° C. To the resultant solution, 50 µL of an AMC substrate solution (0.01 mM) pre-incubated at 37° C. was added, and a fluorescence intensity was measured at an excitation wavelength of 340 nm and a measurement wavelength of 460 nm every 5 minutes for 30 minutes by using a microplate reader (GENio Pro, manufactured by TECAN). The activity in the case without sample was set as 100%, and the relative activity of each sample was calculated. The measurement was repeatedly performed three times for each sample to obtain an average.

The results are illustrated in FIG. 1. Since it was difficult to collect the salmon milt hydrolysate by Papain DF having a high viscosity, its inhibitory activity was not measured. When the serine protease, the aspartic protease and the metalloprotease were used, a DPPIV inhibitory activity was exhibited in any cases, and particularly a high inhibitory activity was shown in the decomposition by the serine protease.

Example 3

Starch Tolerance Test on SD Rat

In this test, SD rats (Slc:SD, 7 weeks old) acclimated for 1 week to the environment of a light-dark cycle of 12 hours (light from 7 a.m. to 7 p.m.), a room temperature of 20 to 24° C., a humidity of 43 to 61%, free feeding (with CRF-1, manufactured by Oriental Yeast Co., Ltd.) and drinking water (tap water) were used. From the evening of the final day of the acclimation, the rats were fasted overnight for 16 hours or more, and, then, were grouped by stratified random sampling based on weight into groups each of 5 rats.

The peptide composition (powder) derived from salmon milt obtained in Example 1 was dissolved in distilled water to prepare a 100 mg/mL solution. This solution was forcedly orally administered at a dose of 100 mg per kg of each SD rat. Alternatively, distilled water was administered at the same dose (in a control group). After administering the test substance, starch (manufactured by Wako Pure Chemical Industries, Ltd.) was dissolved in distilled water to obtain a 20% aqueous solution, so as to be used for loading each rat in an amount of 2 g per kg of the rat. Blood was collected without an anesthesia at four time points of before the starch load, and 30, 60 and 120 minutes after the load. It is noted that a blood glucose level was measured by using a blood glucose self-monitoring device (Nipro Freestyle Freedom, manufactured by Nipro Corporation) for measuring a blood glucose concentration (mg/dL) in the whole blood.

Figure 2:
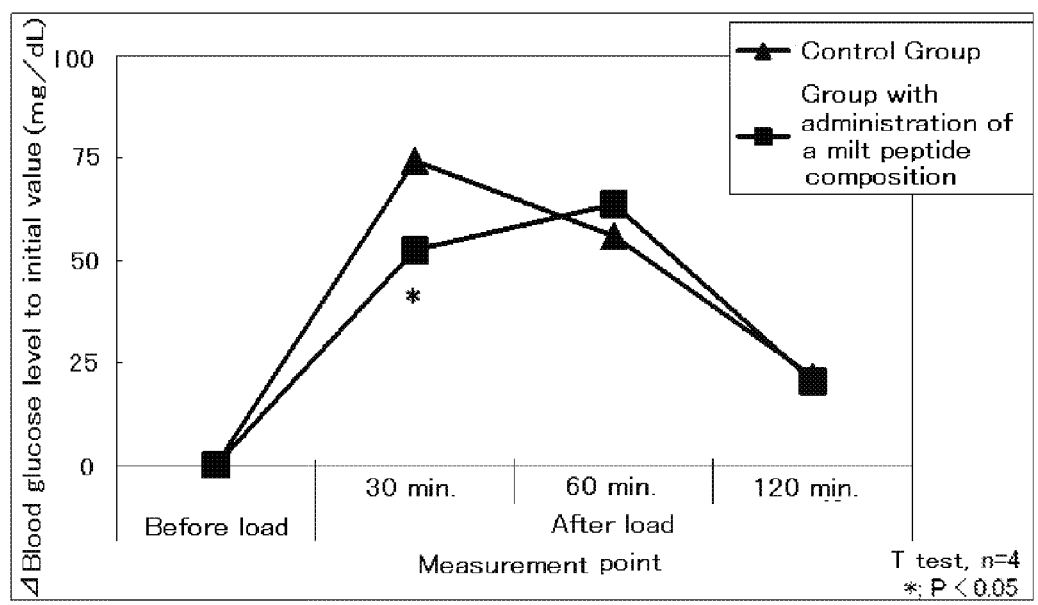
FIG. 2 illustrates the measurement results of the hydrolysates obtained in Example 1 in a starch tolerance test performed on SD rats.

The measurement results are shown in FIG. 2. As a result, as compared with the control group, the increase of blood glucose level was significantly suppressed in a group to which the milt-derived peptide composition was administered. Accordingly, it was revealed that the milt-derived peptide composition has an effect of suppressing the increase of blood glucose level owing to DPPIV inhibition.

Example 4

Measurement of Activity of Peptide Composition

For purpose of examining raw materials, HCl was added to each of milt of chum salmon (salmon milt), protamine, collagen derived from a salmon skin (salmon skin collagen), and milt of Humboldt squid (squid milt) for hydrolysis, and the amino acid composition (mol %) was measured by using an amino acid analyzer JLC-500/V2 (manufactured by JEOL Ltd.). The measurement results are shown in Table 2.

TABLE 2

| Amino Acid | Salmon Milt | Protamine | Salmon Skin Collagen | Squid Milt |
|---|---|---|---|---|
| Tau | 2.1 | 0.1 | 0.0 | 14.0 |
| Asp | 5.0 | 0.2 | 5.1 | 8.8 |
| Thr | 2.9 | 0.1 | 2.3 | 4.3 |
| Ser | 6.4 | 6.8 | 5.1 | 5.2 |
| Glu | 6.7 | 0.2 | 7.5 | 10.2 |
| Gly | 8.6 | 6.9 | 37.6 | 7.9 |
| Ala | 5.3 | 1.9 | 9.9 | 7.6 |
| Val | 2.2 | 4.9 | 1.5 | 0.8 |
| Cys | 2.5 | 0.0 | 0.0 | 3.7 |
| Met | 1.4 | 0.1 | 1.5 | 2.2 |
| Ile | 2.3 | 1.4 | 1.0 | 3.0 |
| Leu | 4.5 | 0.2 | 1.8 | 6.4 |
| Tyr | 1.6 | 0.0 | 0.1 | 2.2 |
| Phe | 2.0 | 0.0 | 1.2 | 2.7 |
| His | 1.3 | 0.0 | 1.3 | 2.0 |
| Lys | 4.7 | 0.2 | 2.7 | 7.1 |
| Arg | 34.0 | 68.6 | 5.2 | 7.1 |
| Hypro | 0.1 | 0.0 | 5.9 | 0.0 |
| Pro | 6.3 | 8.3 | 10.2 | 4.8 |
| Total | 100 | 100 | 100 | 100 |

Milt of chum salmon, milt of squid and collagen peptide derived from a salmon skin were used, respectively, as a material for the hydrolysis, and were combined with the following hydrolytic enzymes, respectively, to obtain peptide compositions (powder) derived from the corresponding materials in the same manner as in Example 1.

Hydrolytic enzyme A

Aroase AP-10 (metalloprotease): chum salmon milt, squid milt

Hydrolytic enzyme B

Alcalase 2.4 L FG (serine protease): chum salmon milt, squid milt

Hydrolytic enzyme C

Protease P "Amano" 3SD (serine protease): chum salmon milt

Hydrolytic enzyme D

Papain (cysteine protease): salmon skin

Each of the peptide compositions thus obtained was dissolved in distilled water in a concentration of 3 mg/mL, the resultant was subjected to a 0.45 µm membrane filter treatment, and the DPPIV inhibitory activity test was performed in the same manner as in Example 2. The results are shown in Table 3.

TABLE 3

| Sample | Name | Material | Hydrolytic Enzyme | DPPIV Inhibition Rate (%) |
|---|---|---|---|---|
| 1 | Salmon Milt Peptide Composition | Chum Salmon Milt | C | 40 |
| 2 | Collagen Peptide | Salmon Skin | D | <20 |
| 3 | Squid Milt Peptide Composition | Humboldt Squid Milt | B | 30 |

Example 5

Method of Concentration of Active Peptide

One hundred mg of each of the peptide composition samples derived from each material obtained in Example 4, respectively, was dissolved in distilled water, the resultant solution was applied to Sep-Pak (registered trademark) column (C18 6 cc: manufactured by Waters) equilibrated with distilled water. Column was then washed with distilled water, and an adsorbed fraction was eluted with moisture ethanol. Each eluate thus obtained was dried with an evaporator to obtain a concentrated fraction of the peptide composition. The eluted fraction thus obtained can be directly used as a DPPIV inhibitory active peptide composition.

Example 6

Search for Active Peptide

Each of the strong DPPIV inhibitory peptides contained in the concentrated fraction of the peptide composition derived from the salmon milt obtained in Example 5 was separated.

Figure 3:
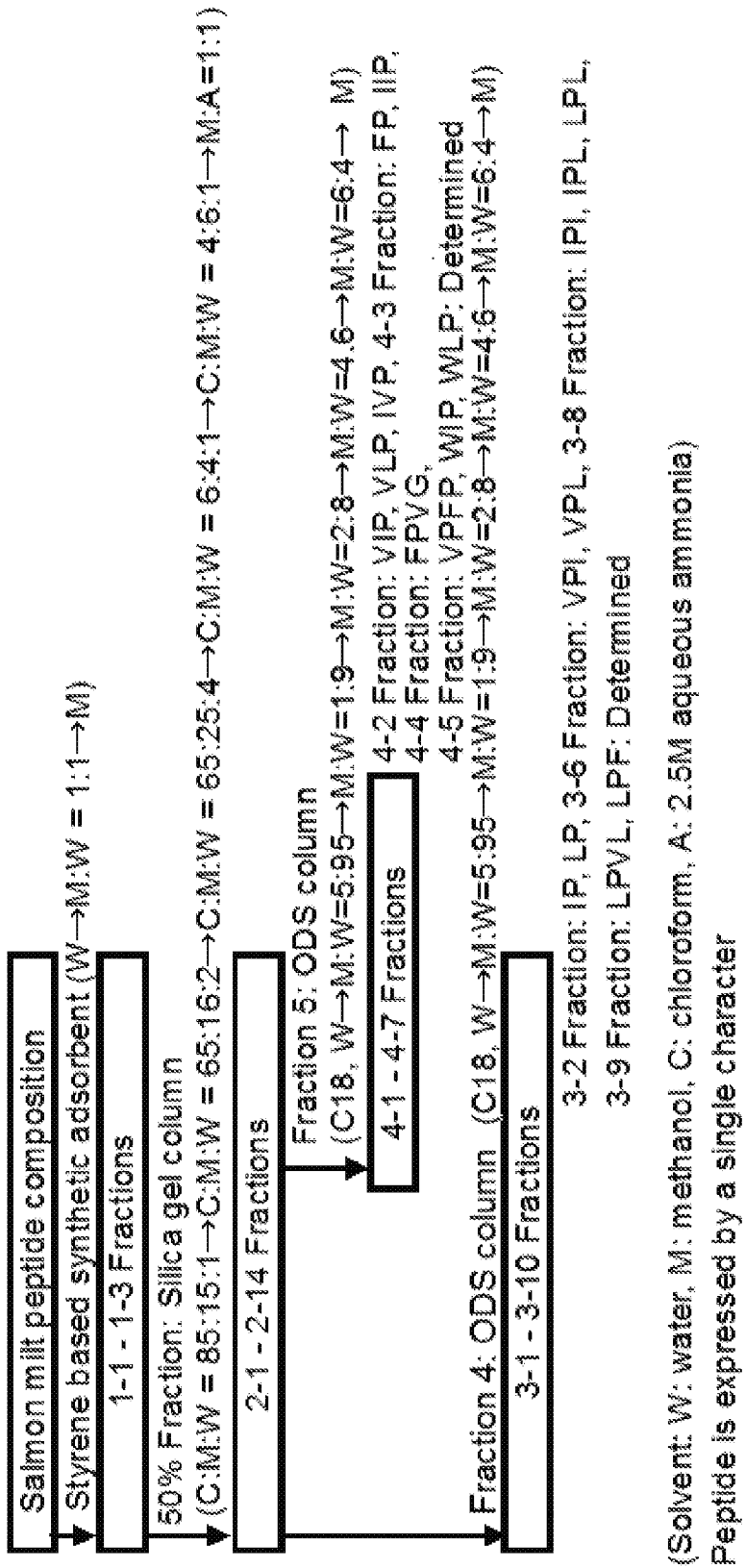
FIG. 3 illustrates a method for purifying a peptide from a hydrolysate of milt.

First, each peptide fraction was separated from the peptide composition as the hydrolysate derived from the salmon milt described in Example 1 according to the method described in FIG. 3. Each peptide fraction thus separated was analyzed by using LC-MS (LCMS-IT-TOF, manufactured by Shimadzu Corporation) under the conditions described below for performing mass spectrum (MS) analysis. Candidate peptides each having a structure presumed by the MS analysis were synthesized by using a peptide synthesizer (Syrol, manufactured by Biotage AB). Each peptide structure was determined by comparing them by using the LC-MS.

(Structure Determination by LCMS-IT-TOF)
<Conditions for HPLC Analysis>
HPLC system: Prominence series manufactured by Shimadzu Corporation (system controller: CBM-20A, auto sampler: SIL-20A, solvent delivery pump: LC-20AB Binary pump, column oven: CTO-20A, PDA detector: SPD-M20A (measurement wavelength: 190 to 700 nm))
Column: Xterra MS C18 3.5 μm, 2.1×100 mm (manufactured by Waters)
Column temperature: 40° C.
Mobile phase A: $H_2O$ (containing 0.1% by volume of TFA, manufactured by Kanto Chemical Co., Inc., for use in LC-MS)
Mobile phase B: methanol (manufactured by Kanto Chemical Co., Inc., for use in LC-MS)
Gradient: 3% by volume of solution B retained for the period from 0 to 15 minutes, linear gradient from 3% by volume of solution B to 60% by volume of solution B for the period from 15 to 45 minutes, and 60% by volume of solution B retained for the period from 45 to 50 minutes
Analysis time: 50 min
Flow rate: 0.1 mL/min
Injection amount: 1 μL
<Detection Conditions for IT-TOF MS>
System: LCMS-IT-TOF manufactured by Shimadzu Corporation (ionization mode: ESI+, atomization gas flow rate: 1.5 L/min, applied voltage: 1.7 kV, CDL temperature: 200° C., BH temperature: 200° C., measurement range MS: m/z 100-1500, MS/MS: 50-1000)

Example 7

Measurement of Activity of Identified Peptides

Each peptide identified by the LC-MS analysis of Example 6 was synthesized and dissolved in distilled water to find the DPPIV inhibitory activity in the same manner as in Example 2. First, each peptide solution was serially diluted to obtain the inhibitory activity at each level, and the 50% inhibitory concentration (IC50 value) of each sample was calculated backward on the basis of a relational expression of the inhibitory activity (%) and a logarithm (Log 10) of the sample concentration. The result of comparison in the DPPIV inhibitory activities among the synthesized peptides is shown in Table 4. Among 18 peptides thus determined, 10 peptides had an 1050 value of 100 μM or less, and had an extremely high DPPIV inhibitory activity.

TABLE 4

| Sequence | Peptide Compound | IC50 Value (μM) |
| --- | --- | --- |
| 1 | Phe-Pro-Val-Gly (FPVG) (SEQ ID NO: 1) | 40 |
| 2 | Ile-Pro-Leu (IPL) | 26 |
| 3 | Leu-Pro-Val-Leu (LPVL) (SEQ ID NO: 2) | 46 |
| 4 | Val-Pro-Phe-Pro (VPFP) (SEQ ID NO: 3) | 22 |
| 5 | Ile-Pro (IP) | 66 |
| 6 | Leu-Pro (LP) | >100 |
| 7 | Val-Pro-Ile (VPI) | 3 |
| 8 | Val-Pro-Leu (VPL) | 19 |
| 9 | Ile-Pro-Ile (IPI) | 3 |
| 10 | Leu-Pro-Leu (LPL) | 82 |
| 11 | Leu-Pro-Phe (LPF) | 88 |
| 12 | Phe-Pro (FP) | >100 |
| 13 | Val-Ile-Pro (VIP) | >100 |
| 14 | Val-Leu-Pro (VLP) | >100 |
| 15 | Ile-Val-Pro (IVP) | >100 |
| 16 | Ile-Ile-Pro (IIP) | >100 |
| 17 | Trp-Ile-Pro (WIP) | >100 |
| 18 | Trp-Leu-Pro (WLP) | >100 |

Example 8

Measurement of Content of Active Peptide

Each concentrated fraction of the peptide composition obtained from each of the materials in Example 4 was dissolved in distilled water in a concentration of 2 mg/mL, and the resultant solution was subjected to a 0.45 μm membrane filter treatment to be used for measuring the content of an active peptide. A similar peptide composition was prepared based on a by-product as a residual resulting from DNA extraction and separation in DNA production from chum salmon milt as a raw material, and the content of an active peptide therein was measured. Among the peptides identified as described above, IP, VPI, VPL, IPI, LPL, LPI and IPL were quantitatively determined by using JMS LCmate (manufactured by JEOL Ltd.) under conditions A described below. Among the peptides thus determined as described above, FPVG (SEQ ID NO: 1), LPVL (SEQ ID NO: 2), VPFP SEQ ID NO: 3) and LPF were quantitatively determined under conditions B described below. The result of the quantitative determination thus obtained and the IC50 value (μM) of the DPPIV inhibitory activity of each of the peptides identified in the above-described example were used to calculate an activity contribution ratio in accordance with the following equation:

Contribution ratio=(Content of a determined peptide per g of a peptide composition/(IC50 value (µM) of the determined peptide×molecular weight of the determined peptide/1000))/(1000/IC50 value (µg/mL) of the peptide composition)×100

(Conditions A for quantitative analysis of determined peptide)
<Conditions for HPLC Analysis>
HPLC system: Alliance Waters 2695 (manufactured by Waters)
Column: Discovery (registered trademark) HS F5, 5 µm, 2.1×250 mm (manufactured by SUPELCO, Inc.)
Mobile phase A: $H_2O$ (containing 0.1% by volume of formic acid and 0.01% by volume of TFA, manufactured by Kanto Chemical Co., Inc., for use in LC-MS)
Mobile phase B: methanol (manufactured by Kanto Chemical Co., Inc., for use in LC-MS)
Gradient: linear gradient from 40% by volume of solution B to 80% by volume of solution B for the period from 0 to 30 minutes, and 80% by volume of solution B retained for the period from 30 to 35 minutes
Analysis time: 35 min
Flow rate: 0.2 mL/min
Injection amount: 5 µL
Analysis time: 29 min
Flow rate: 0.2 mL/min
Injection amount: 54
<Detection Conditions for MS>
System: JMS-LCmate (manufactured by JEOL Ltd.)
Ionization mode: ESI+, SIM measuring ion: m/z: 376.2, 419.2, 441.3, 459.3 The result of the quantitative analysis test [Content (mg/g) of active peptide in each peptide composition (1 g)] is shown in Table 5. Regarding the collagen peptide derived from a salmon skin having a low DPPIV inhibitory activity, the determined peptides were not detected. On the other hand, in the peptide compositions derived from squid milt found to have a DPPIV inhibitory activity, the aforementioned active peptides were detected, and it was revealed that these active peptides make contribution to the DPPIV inhibitory activity of these peptide compositions. It was found that a peptide composition containing a plurality of peptides from these active peptides has the DPPIV inhibitory activity.

The active contribution ratios of the active peptides in the salmon milt peptide compositions may be in a range as shown in Table 6.

TABLE 5

| Sequence | Peptide Compound | Salmon Milt + Hydrolytic Enzyme C | Salmon Milt + Hydrolytic Enzyme B | DNA By-product + Hydrolytic Enzyme C | Squid Milt + Hydrolytic Enzyme B | Salmon Milt + Hydrolytic Enzyme A | Squid Milt + Hydrolytic Enzyme A | Salmon Skin + Hydrolytic Enzyme D (Collagen Peptide) |
|---|---|---|---|---|---|---|---|---|
| 1 | FPVG (SEQ ID NO: 1) | 0.10 | — | 0.12 | — | 0.03 | — | — |
| 2 | IPL | 0.05 | 0.05 | 0.02 | 0.04 | 0.02 | — | — |
| 3 | LPVL (SEQ ID NO: 2) | 0.04 | 0.12 | 0.05 | 0.04 | — | 0.11 | — |
| 4 | VPFP (SEQ ID NO: 3) | 0.10 | 0.04 | 0.13 | — | — | 0.11 | — |
| 5 | IP | 1.27 | 0.03 | 0.39 | 0.05 | 1.14 | 0.27 | — |
| 7 | VPI | 0.06 | 0.04 | 0.07 | — | 0.03 | — | — |
| 8 | VPL | 0.16 | 0.06 | 0.24 | 0.04 | 0.04 | 0.15 | — |
| 9 | IPI | 0.03 | 0.05 | 0.06 | — | 0.02 | 0.05 | — |
| 10 | LPL | 0.04 | 0.02 | — | 0.04 | — | — | — |
| 11 | LPF | 0.10 | 0.05 | 0.05 | 0.09 | — | — | — |

It is noted that a symbol "—" shown in this table means N.D. (not detected).

<Detection Conditions for MS>
System: JMS-LCmate (manufactured by JEOL Ltd.)
Ionization mode: ESI+, SIM measuring ion: m/z: 229.2, 328.2, 342.2
(Conditions B for Quantitative Analysis of Determined Peptide)
<Conditions for HPLC Analysis>
HPLC system: Alliance Waters 2695 (manufactured by Waters)
Column: XTerra (registered trademark) Phenyl 3.5 µm, 4.6×100 mm column (manufactured by Waters)
Mobile phase A: $H_2O$ (containing 0.1% by volume of formic acid and 0.01% by volume of TFA, manufactured by Kanto Chemical Co., Inc., for use in LC-MS)
Mobile phase B: methanol (manufactured by Kanto Chemical Co., Inc., for use in LC-MS)
Gradient: 40% by volume of solution B retained for the period from 0 to 4 minutes, linear gradient from 40% by volume of solution B to 60% by volume of solution B for the period from 4 to 24 minutes, and 60% by volume of solution B retained for the period from 24 to 29 minutes

TABLE 6

| Sequence | Peptide Compound Salmon Milt Peptide Composition (IC50 Value = 786 µg/mL) | Content of Peptide in 1 g of Composition (mg/g) | Activity Contribution Ratio (%) | Activity Contribution Ratio: Lower Limit (%) | Activity Contribution Ratio: Upper Limit (%) |
|---|---|---|---|---|---|
| 1 | FPVG (SEQ ID NO: 1) | 0.10 | 0.4 | 0.01 | 5 |
| 2 | IPL | 0.05 | 0.4 | 0.01 | 5 |
| 3 | LPVL (SEQ ID NO: 2) | 0.04 | 0.2 | 0.005 | 5 |
| 4 | VPFP (SEQ ID NO: 3) | 0.10 | 0.8 | 0.01 | 10 |
| 5 | IP | 1.27 | 6.6 | 0.01 | 30 |
| 7 | VPI | 0.06 | 5.1 | 0.01 | 25 |
| 8 | VPL | 0.16 | 2.0 | 0.01 | 20 |

TABLE 6-continued

| Sequence | Peptide Compound Salmon Milt Peptide Composition (IC50 Value = 786 µg/mL) | Content of Peptide in 1 g of Composition (mg/g) | Activity Contribution Ratio (%) | Activity Contribution Ratio: Lower Limit (%) | Activity Contribution Ratio: Upper Limit (%) |
|---|---|---|---|---|---|
| 9 | IPI | 0.03 | 2.5 | 0.01 | 20 |
| 10 | LPL | 0.04 | 0.1 | 0.001 | 5 |
| 11 | LPF | 0.10 | 0.2 | 0.005 | 5 |

As shown in Table 5, as the common components by all the hydrolytic enzymes, each peptide composition contained Ile-Pro (IP) as a dipeptide and Val-Pro-Leu (VPL) as a tripeptide. Regarding the peptide compounds obtained by using the serine protease, in addition to Ile-Pro (IP) and Val-Pro-Leu (VPL), Ile-Pro-Leu (IPL) and Leu-Pro-Val-Leu (LPVL, SEQ ID NO: 2) were contained. Regarding the salmon milt-derived peptide compositions, although the hydrolytic enzyme was changed, in addition to Ile-Pro (IP) and Val-Pro-Leu (VPL), Ile-Pro-Leu (IPL) was contained.

Example 9

DPPIV Inhibitory Activity and Peptide Content of Peptide Composition Derived from Milt of Each Fishery Product A peptide composition was obtained in the same manner as in Example 1 by using milt of each fishery product (chum salmon, pink salmon, herring, pacific cod, skipjack, yellowtail (young yellowtail) and squid) as a raw material. Specifically, water was added to 10 g of a ground product of milt of each fishery product to adjust the resultant solution to pH 8.0; 0.016 g of the enzyme (Protease P "Amano" 3SD) was added thereto; and an enzymatic decomposition reaction was performed at 50° C. for 5 hours. After the reaction, the reaction solution thus obtained was heated to 90° C. to inactivate the enzyme, and after cooling the solution, the resultant was filtered by using Celite. The filtrate was freeze-dried to obtain a powder of a DPPIV inhibitory peptide composition.

The peptide composition wad dissolved in distilled water, and the resultant was subjected to a 0.45 µm membrane filter treatment to be used for measuring the DPPIV inhibitory activity and the content of active peptide.

The DPPIV inhibitory activity was measured by using a partly modified DPPIV Drug Discovery Assay Kit (manufactured by Enzo Life Sciences, Inc.). As a substrate of a DPPIV enzyme, an AMC substrate (H-Gly-Pro-amino-4-methylcoumarin, BML-P189-9090; manufactured by Biomol) was used; as an enzyme, DPPIV (Human, recombinant; manufactured by Biomol) was used; and as a control inhibitor, Diprotin A (manufactured by Peptide Institute Inc.) was used. Specifically, in a 96-well plate, 25 µL of a 50 mM Tris buffer (pH 7.5), 10 µL of the peptide composition (3, 10 or 20 mg/mL) and 50 µL of an AMC substrate solution (0.01 mM) were added and mixed, and the resultant mixture was pre-incubated at 37° C. To the resultant solution, 15 µL of a DPPIV (0.002 mU/µL) solution was added to start a reaction, and a fluorescence intensity was measured at an excitation wavelength of 340 nm and a measurement wavelength of 460 nm every 5 minutes for 30 minutes by using a microplate reader (GENio Pro, manufactured by TECAN). On the basis of the value of relative activity of each sample calculated by defining that the activity without sample was 100%, an $IC_{50}$ value (µM) of the DPPIV inhibitory activity was calculated.

Figure 4:
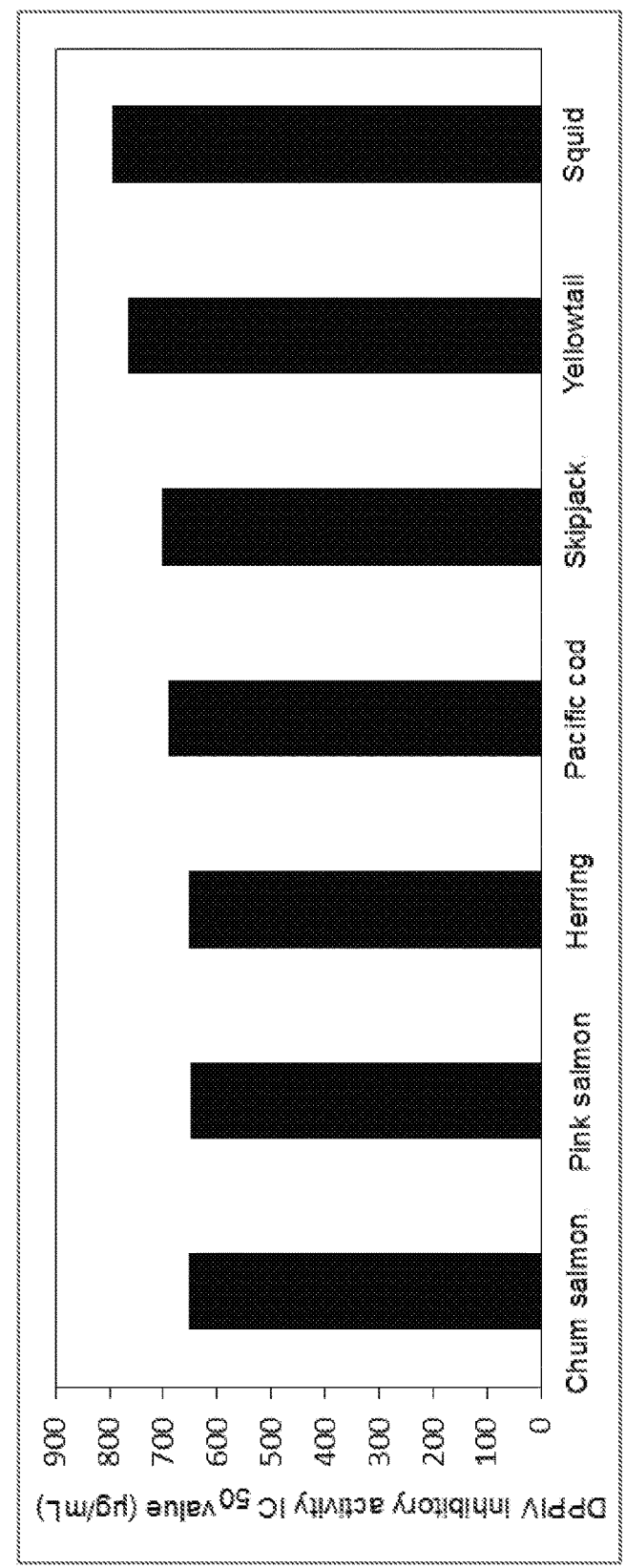
FIG. 4 illustrates the measurement results of DPPIV inhibitory activity of hydrolysates obtained in Example 9.

The results are illustrate in FIG. 4. Although there is a difference depending upon the kind of fish, a high DPPIV inhibitory activity was recognized by all the kinds of fish used herein as the samples.

Next, an active peptide was quantitatively determined in each of the peptide compositions. The quantitative determination was performed by using Xevo-TQD (manufactured by Waters) under the following conditions C:

(Conditions C for Quantitatively Determining Active Peptide)

<Conditions for UPLC Analysis>
UPLC system: ACQUITY (manufactured by Waters)
Column: ACQUITY HSS PFP, 1.8 .mu.m, 2.1.times.150 mm (manufactured by Waters)
Mobile phase A: $H_2O$ (containing 0.1% by volume of formic acid, manufactured by Kanto Chemical Co., Inc., for use in LC-MS)
Mobile phase B: methanol (manufactured by Kanto Chemical Co., Inc., for use in LC-MS)
Gradient: linear gradient from 20% by volume of solution B to 72% by volume of solution B for the period from 0 to 15 minutes, and 80% by volume of solution B retained for the period from 15 to 20 minutes
Analysis time: 20 min
Flow rate: 0.2 mL/min
<Detection Conditions for MS>
System: Xevo-TQD (manufactured by Waters)
Ionization mode: ESI+, MS MRM measurement precursor/product ions (Q1/Q3): IP=229.1/86.0, VPI=328.2/229.1, VPL=328.2/229.1, IPI=342.1/229.1, LPL=342.1/229.1, IPL=342.2/229.1, LPF=376.1/263.2, FPVG (SEQ ID NO: 1)=419.2/120.0, LPVL (SEQ ID NO: 2)=441.3/169.1, VPFP (SEQ ID NO: 3)=459.2/197.1

The result of the quantitative determination [Content (mg/100 g) of active peptide in each peptide composition] is shown in Table 7. The DPPIV inhibitory active peptides were detected in all the kinds of fish used herein as the samples.

TABLE 7

| Sequence | Peptide Compound | Chum Salmon | Pink Salmon | Herring | Pacific Cod | Skipjack | Yellowtail | Squid |
|---|---|---|---|---|---|---|---|---|
| 1 | FPVG (SEQ ID NO: 1) | 3.2 | 4.6 | 1.4 | 11.0 | 2.4 | 1.9 | 1.4 |
| 2 | IPL | 0.7 | 0.6 | 0.9 | 0.4 | 0.2 | 0.2 | 0.1 |
| 3 | LPVL (SEQ ID NO: 2) | 0.6 | 0.4 | 0.3 | 0.2 | 0.2 | 0.2 | 0.1 |

TABLE 7-continued

| Sequence | Peptide Compound | Chum Salmon | Pink Salmon | Herring | Pacific Cod | Skipjack | Yellowtail | Squid |
|---|---|---|---|---|---|---|---|---|
| 4 | VPFP (SEQ ID NO: 3) | 4.7 | 1.9 | 12.0 | 2.7 | 3.1 | 3.1 | 1.5 |
| 5 | IP | 83.6 | 88.0 | 39.2 | 93.0 | 69.4 | 61.4 | 46.9 |
| 7 | VPI | 0.3 | 0.1 | 0.3 | 0.1 | 0.1 | 0.1 | 0.1 |
| 8 | VPL | 1.1 | 0.9 | 1.5 | 0.7 | 0.5 | 0.5 | 0.4 |
| 9 | IPI | 0.2 | 0.2 | 0.2 | 0.2 | 0.1 | 0.1 | 0.1 |
| 10 | LPL | 2.5 | 2.4 | 2.7 | 1.6 | 1.0 | 1.2 | 0.6 |
| 11 | LPF | 2.9 | 5.5 | 3.9 | 3.4 | 0.9 | 1.4 | 1.2 |

The invention claimed is:

1. A composition for inhibiting dipeptidyl peptidase-IV (DPPIV), comprising:

(i) a hydrolysate of a protein source derived from milt of a fishery product, wherein the hydrolysate comprises at least one peptide compound selected from the group consisting of Ile-Pro-Leu and salts thereof; and (ii) at least one component selected from the group consisting of a carrier, an excipient, a diluent and additives.

2. The composition according to claim 1, wherein the fishery product is one or more of salmon, pink salmon, herring, pacific cod, skipjack, yellowtail (young yellowtail) and squid.

3. The composition according to claim 1, wherein the at least one peptide compound has the effect of inhibiting an increase in blood glucose level by the DPPIV inhibitory activity.

4. The composition according to claim 1, wherein the protein source derived from the milt of a fishery product is a protein source comprised in an extraction residue obtained as a by-product in extraction of protamine and/or DNA from milt of a fishery product.

5. The composition according to claim 1, wherein the composition is formulated for medical use.

6. The composition according to claim 1, wherein the composition is formulated as a food product.

7. The composition according to claim 1, wherein the composition is formulated as a pet food product.

8. The composition according to claim 1, further comprising at least one peptide compound selected from the group consisting of Phe-Pro-Val-Gly (SEQ ID NO:1) and salts thereof, Leu-Pro-Val-Leu (SEQ ID NO:2) and salts thereof, and Val-Pro-Phe-Pro (SEQ ID NO:3) and salts thereof.

9. A composition for inhibiting dipeptidyl peptidase-IV (DPPIV), comprising:
 (i) as a DPPIV inhibitory active component, at least one peptide compound selected from the group consisting of Phe-Pro-Val-Gly (SEQ ID NO:1) and salts thereof, Ile-Pro-Leu and salts thereof, and
 (ii) at least one component selected from the group consisting of a carrier, an excipient, a diluent, and additives.

10. The composition according to claim 9, having an effect of inhibiting an increase in blood glucose level by the DPPIV inhibitory activity.

11. The composition according to claim 9, further comprising at least one peptide compound selected from the group consisting of Phe-Pro-Val-Gly (SEQ ID NO:1) and salts thereof, Leu-Pro-Val-Leu (SEQ ID NO:2) and salts thereof, and Val-Pro-Phe-Pro (SEQ ID NO:3) and salts thereof.

12. The composition according to claim 9, wherein the composition is formulated for medical use.

13. The composition according to claim 9, wherein the composition is formulated as a food product.

14. The composition according to claim 9, wherein the composition is formulated as a pet food product.

15. A peptide compound selected from the group consisting of Ile-Pro-Leu and a salt thereof.

* * * * *